US010352696B2

(12) United States Patent
Silverman

(10) Patent No.: US 10,352,696 B2
(45) Date of Patent: *Jul. 16, 2019

(54) ULTRASONIC CATHODIC PROTECTION TEST STATION

(71) Applicant: BERKELEY SPRINGS INSTRUMENTS LLC, Cumberland, MD (US)

(72) Inventor: Eugene B. Silverman, Cumberland, MD (US)

(73) Assignee: BERKELEY SPRINGS INSTRUMENTS LLC, Cumberland, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/255,800

(22) Filed: Sep. 2, 2016

(65) Prior Publication Data

US 2017/0067736 A1    Mar. 9, 2017

Related U.S. Application Data

(60) Provisional application No. 62/213,813, filed on Sep. 3, 2015.

(51) Int. Cl.
*G01N 17/04*    (2006.01)
*G01N 29/28*    (2006.01)
(Continued)

(52) U.S. Cl.
CPC ........... *G01B 17/02* (2013.01); *G01N 17/043* (2013.01); *G01N 27/021* (2013.01); *G01N 29/07* (2013.01);
(Continued)

(58) Field of Classification Search
CPC .... G01N 17/046; G01N 17/043; G01N 29/07; G01N 29/223; G01N 29/2468; G01B 17/02
(Continued)

(56) References Cited

U.S. PATENT DOCUMENTS 3,056,284 A * 10/1962 Marsh .................... G01N 17/04
                                                                324/700
3,747,398 A *  7/1973 Rathburn ............... G01B 17/00
                                                                73/617
(Continued)

FOREIGN PATENT DOCUMENTS

WO      2014/193808 A1    12/2014

OTHER PUBLICATIONS

Extended European Search Report, dated Apr. 11, 2019, for European Application No. 16843069.2.

*Primary Examiner* — Lisa M Caputo
*Assistant Examiner* — Rose M Miller
(74) *Attorney, Agent, or Firm* — Birch, Stewart, Kolasch & Birch, LLP

(57) ABSTRACT

Ultrasonic transducers are imbedded into sacrificial metal coupons which are located in the vicinity of underground or aboveground structures, such as a pipe or tank, which allow for the measurement of the effectiveness of impressed current cathodic protection systems and can be used to determine the corrosion rate of the structure that is being protected. When excited by a pulser-receiver excitation pulse, the ultrasonic transducers can be used to determine the thickness of the coupon and its rate of change over time. The sacrificial metal coupon ultrasonic transducer assembly can be located in the vicinity of underground piping, under or inside of a tank, underground or underwater, or inserted into structures where absolute material loss values or material loss rate of change is being monitored.

2 Claims, 8 Drawing Sheets

(51) Int. Cl.
*G01N 29/07* (2006.01)
*G01B 17/02* (2006.01)
*G01N 27/02* (2006.01)

(52) U.S. Cl.
CPC ....... *G01N 29/28* (2013.01); *G01N 2291/011* (2013.01); *G01N 2291/0258* (2013.01); *G01N 2291/02854* (2013.01)

(58) Field of Classification Search
USPC ..... 73/627, 597, 598, 590, 594, 601, 86, 87, 73/432.1
See application file for complete search history.

(56) References Cited

U.S. PATENT DOCUMENTS

| | | | |
|---|---|---|---|
| 5,636,959 A * | 6/1997 | Kroell | B63B 17/023 114/201 R |
| 5,728,943 A | 3/1998 | Colter, Jr. et al. | |
| 8,521,453 B1 | 8/2013 | Silverman et al. | |
| 2002/0078752 A1* | 6/2002 | Braunling | G01N 17/04 73/627 |
| 2002/0148293 A1* | 10/2002 | Little | G01N 29/11 73/579 |
| 2004/0055391 A1 | 3/2004 | Douglas et al. | |
| 2015/0002132 A1 | 1/2015 | Brelsford et al. | |
| 2016/0109413 A1* | 4/2016 | Bonadies, Jr. | G01N 29/07 73/598 |
| 2017/0067736 A1* | 3/2017 | Silverman | G01B 17/02 |

* cited by examiner

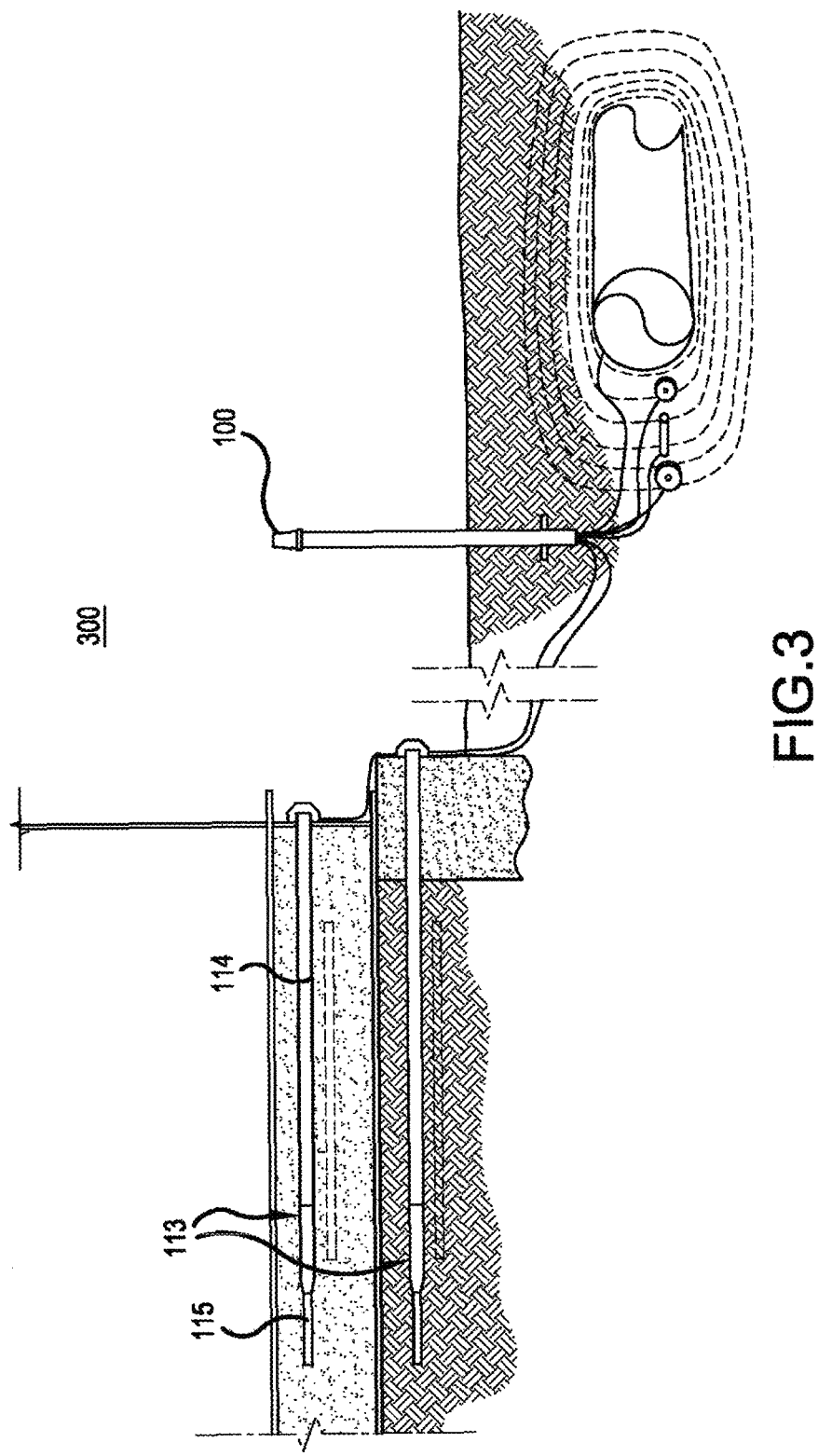

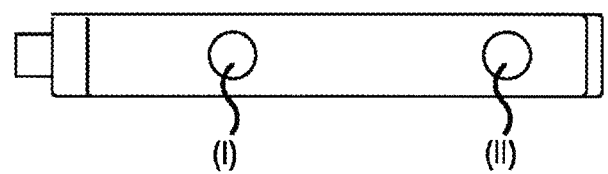
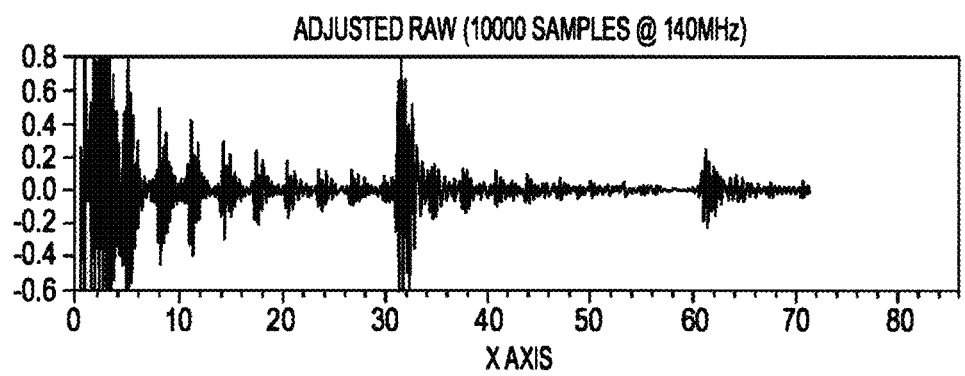
FIG.4A

ULTRASONIC CATHODIC PROTECTION TEST STATION

CROSS REFERENCE TO RELATED APPLICATIONS

This application claims the benefit of U.S. provisional application No. 62/213,813, filed Sep. 3, 2015, the contents of which are incorporated herein by reference.

FIELD OF INVENTION

This application relates to the use of ultrasound transducers imbedded into a sacrificial anode that is located in the vicinity of an underground structure, such as a pipe or tank, for measuring the effectiveness of impressed current cathodic protection systems and determining the corrosion rate of the structure that is being protected.

BACKGROUND

Buried or immersed metal structures, such as pipes and tanks, are exposed to an electrochemical corrosion process in the underground environment. The metal structure becomes an electrode and the soil an electrolyte so that an electrolytic cell is formed causing the corrosion of the buried structure. Some corrosion arises from naturally occurring processes at specific locations on the underground structure involving electrical current flow into the ambient soil electrolyte from sites acting as anodes via the corrosion reaction. Current will flow to specific locations on underground structures acting as cathodes where reduction reactions occur. Corrosion can also be caused or accelerated by voltages applied to a local region of the pipe by manmade structures, including local transit systems, overhead subsurface power distribution systems, and industrial plants.

There are generally two methods to protect the underground structure from corroding. These methods are referred to as "cathodic protection." The first method is to attach sacrificial anodes onto or near the underground structure being protected, and the second is to install an impressed current system that generates a DC voltage and a low constant current in the specific vicinity of the structure being protected.

Sacrificial anodes are pieces of metal more electrically active than the underground structure that can be attached to the underground structure for corrosion protection. Because these anodes are more active than the underground structure, the corrosive current will exit from the sacrificial anodes rather than from the underground structure. Thus, the underground structure is protected while the attached anode is sacrificed. Depleted anodes must be replaced for continued corrosion protection of the underground structure.

An impressed current system uses a rectifier that converts alternating current to direct current. This current is sent through an insulated wire to the anodes, which are metal bars buried in the soil near the underground structure being protected. The current flows through the soil to the underground structure and returns to the rectifier through an insulated wire attached to the underground structure. The underground structure is protected because the current going to the underground structure overcomes the corrosion-causing current normally flowing away from it.

With a cathodic protection system, industry accepted criteria involve the measurement of the electrochemical potential of the structure to establish the level of cathodic protection sufficient to mitigate corrosion of the buried metal structure. The ordinary practice to determine the necessary level of cathodic protection is to measure the potential difference between the buried structure, which is an electrode, and a reference electrode placed, at grade, in contact with the soil, which is an electrolyte. However, when this measurement is taken while the cathodic protection system is operating, a voltage drop through the soil due to the cathodic protection current, referred to as the IR (voltage) drop, causes an error in the potential measurement.

In order to measure a potential that is free of IR drop, it is common to measure the potential immediately following interruption of the cathodic protection current. The instantaneous voltage drop which occurs immediately after the cathodic protection is turned off is equal to the IR drop caused by the interrupted cathodic protection current. Because the electrochemical interface of the protected structure has a capacitive component, the potential of that interface does not change immediately following interruption as does the IR drop. Therefore, the potential measured immediately following interruption of the cathodic protection current, when current, I, is zero, is the potential of the protected structure free of IR drop. This potential is referred to as off-potential.

Problems arise in interrupting the cathodic protection. Extremely long buried pipelines have multiple cathodic protection stations, all of which must be interrupted simultaneously, or interrupted using a non-synchronous method in which all of the IR drops are summed. Galvanic cathodic protection systems are not designed to be interrupted because the anodes are typically directly connected to the protected structure. Additionally, second-party cathodic protection systems that are either unknown or cannot be interrupted may be present in the area. Other problems exist, also, such as stray current effects, e.g., from power distribution systems, dc transit systems, etc., that are not interruptable, and rapid IR transients, which immediately follow interruption. For instance, AC current magnetic fields created in the vicinity of high voltage power lines can propagate into the earth and induce corrosion. This is known as AC-induced corrosion. Such corrosion on cathodically protected underground pipelines is commonly the result of a combined action of the induced AC voltage, the cathodic protection conditions, a piping coating defect and the chemical and physical conditions of the soil. As a result, both DC and AC current fields can influence corrosion of underground structures.

In order to avoid the problems associated with interruption of the entire cathodic protection system, "coupons" are used to monitor the level of cathodic protection on buried metal structures such as pipes. The coupon is a bare metal sample having substantially the same metallurgical attributes as the pipe or other structure being monitored. The coupon is placed in the soil near the pipe and connected to the pipe. Therefore, the coupon is exposed to the same cathodic protection current source as the pipe. The connection between the pipe and the coupon is interrupted for a time period, during which time the potential difference between the coupon and a reference electrode is measured. The pipe's cathodic protection is never interrupted, since only the pipe-to-coupon connection is interrupted. The coupon's potential simulates the potential of a pipe coating defect of a similar surface area as the coupon. The coupon's potential can be measured without interrupting the cathodic protection to the pipe, and therefore without some of the problems inherent in interrupting the entire cathodic protection system. In addition, once the coupon is interrupted, it is an isolated, small piece of metal in the soil and stray currents are eliminated from its surface. In contrast, stray currents are generally not eliminated from a pipeline upon interruption of the entire cathodic protection system.

Despite the existence of a significant number of devices for determining the effectiveness of cathodic protection, the need exists for a simple, inexpensive and accurate measuring device. In the description provided above, the coupon serves as a simulation of the behavior of the underground structure that is being protected. The coupon is used for measuring changes in electrical potential near and in the vicinity of the underground structure that is being protected. The changes in electrical potential are characteristically "noisy." That is, the changes in the electrical potentials or the resistance of a coupon are not always consistent and are affected by temperature variations, the presence of stray currents themselves, instrumentation calibration challenges and operator error. There is a need for coupons that are not impacted by environmental or operator data-acquisition variables; coupons that can be measured with more precision and accuracy.

SUMMARY

The present invention solves the foregoing problems by providing a coupon imbedded with one or more ultrasonic transducers that can determine the thickness of the coupon and can be energized and read from the surface by an operator with a suitable ultrasound pulse/receiver instrument. The piezoelectric ultrasound transducer converts the pulse of electrical energy into an acoustic pressure wave (sound). The pressure wave is coupled to the surface of a plate via fluid in a reservoir, or by an equivalent acoustic coupler. Most of the energy (sound) is reflected from the front surface of the plate due to the acoustic impedance discontinuity. Some energy enters the plate and travels through the plate and is reflected from the back surface of the plate back towards the front surface. Some of the reflected energy leaves the front of the plate and some is reflected towards the back surface of the plate. This reflection process continues. Energy is lost from the plate boundary surfaces for each reflection. Energy lost at the front of the plate travels back towards the ultrasound transducer where it is received and converted back to electrical energy. The electrical pulses received represent the two way acoustic front-to-back acoustic travel times. The thickness of the plate can be estimated by measuring the pulse to pulse travel time and knowing the velocity of sound in the plate under test. By searching for a reduction in the plate thickness, plate corrosion or pitting can be located.

The transducers can be positioned directly underneath the coupon's surface and can, on operator demand, measure the thickness of the coupon. The coupon's thickness will change as the metallurgy of the underground structure changes in a way that alters the thickness of the coupon material as well. This information provides a direct rather than an inferred measure of rate of material loss due to any corrosion activity that may be occurring with the underground structure under protection.

In one of many possible embodiments of the invention, the system includes two "smart ultrasonic coupons" or for simplicity "probes." Each ultrasonic transducer has 2 wires. Each probe has 2 to 3 transducers; therefore, there are 4 to 6 transducer wires that allow each transducer to be activated from the surface by an operator. There is an additional ground wire available to the operator for each probe. Additionally, one probe has a reference electrode with a wire connected to it and available at the surface for operator access. A wire also is connected to the underground structure and is also available to the operator at the surface. This arrangement provides the operator with all the functionality associated with traditional cathodic protection test stations. However, the addition of the ultrasonic coupons located within each probe provides the operator with the added ability to directly monitor metal loss, a more accurate assessment of underground structural integrity.

Coupons with imbedded ultrasonic transducers optionally but preferably can include one or more of the following features:

1. Frequencies of the probe can be selected based on the required thickness of the coupon.
2. The metallic, sacrificial material within each probe can be changed to match that of the structure being monitored.
3. The area of the exposed surface of the coupon can be modified to accommodate increased sensitivity to DC current (10 $cm^2$) or AC current (1 $cm^2$).
4. The distance of the transducer from the coupon can be changed to improve the quality of the ultrasonic return and better decipher the echo-to-echo pulses needed to determine coupon thickness and change of thickness sensitivity.
5. Each transducer within the probe can generate a bulk wave that can be received by any adjacent transducer. Such a bulk wave can be used to evaluate local changes in the coupon surface that might not be detected if not present directly above an individual transducer.
6. Signal processing techniques can be applied to the activation and signal reception of each ultrasonic transducer such that "chirp" signals can be generated, received and analyzed in addition to traditional pulse-echo signals.

Non-limiting examples of applications for which a cathodic protection test station of the present invention can be used include:

1. Aboveground or belowground tanks
2. Aboveground or belowground pipes and piping
3. Submerged structures such as those for bridges and buildings
4. Underground pilings, tunnels, and related infrastructure The ultrasonic cathodic protection test station of the present invention solves many of the monitoring accuracy and handling problems through the use of one or more piezoelectric ultrasonic testing (UT) transducers integrated into a sacrificial coupon. UT transducers are known to the non-destructive testing industry as one of the most accurate, repeatable and precise methods of determining material degradation and material loss. UT transducers have not been used in connection with sacrificial coupons, at least in part, because of the inability to effectively secure an ultrasonic transducer to a coupon for long periods of time. The connection interface between the UT transducer and the coupon changes over time, e.g., by evaporation or other chemical or physical changes, and as a result the ability of the transducer to transfer acoustic energy to the coupon is affected. The present invention solves this problem, and as a result UT transducers can be used to measure and monitor changes over time in a sacrificial coupon.

The present invention further solves the foregoing problems by providing a coupon-ultrasonic measurement system combined with one or more transducers for determining material loss. The system includes a sacrificial coupon; one or more transducers supported under the sacrificial coupon and responsive to electrical energy from a pulser/receiver; remotely-located drive circuitry for energizing and receiving energy from the transducers; an attachment mechanism for use in above ground storage tanks for positioning the sacrificial coupon and transducer assembly under the tank; an a cabling mechanism for use adjacent to an underground pipe or underground tank; and processing and memory means for producing the excitation pulse, receiving the transmitted pulse, processing the signal to determine material thickness, and storing the resultant material thickness values for display and tracking.

A sacrificial metal coupon is provided with one or more ultrasonic transducers which, when excited by a pulser-receiver excitation pulse, determines the thickness of the coupon and its rate of change over time. The sacrificial metal coupon ultrasonic transducer assembly can be placed adjacent to a pipe, under or inside of a tank, underground or underwater, or inserted adjacent to structures where absolute material loss values or material loss rate of change is being monitored. In order to characterize the type of metal loss due to corrosion or erosion, the excitation pulse can be a pulse-echo or chirp pulse and one transducer can insonify the coupon and the second transducer can receive the transmission a fixed distance away for further analysis. The use of ultrasound to measure metal loss in a sacrificial coupon minimizes the inaccuracy of traditional sacrificial coupon metal loss measurements and provides for a more convenient and safe method for determining coupon integrity.

The test station's coupon-ultrasonic material measurement system can also be used to evaluate the effectiveness of chemical inhibitors which are used to mitigate the impact of localized electrical interference by changing the resistance characteristics of the surrounding earth electrolyte conditions. The UT test station, in its standard configuration, consists of a reference electrode, e.g., CuCuSo4 material, used to simultaneously measure the effectiveness of neighboring electromagnetic fields generated by cathodic protection impressed current systems.

One aspect of the invention is a corrosion coupon probe including: two or more coupon bodies adapted for receiving sensors, receivers, transmitters, electrical components, and cabling for altering the distance of the corrosion coupons from the primary aboveground test station; cabling connected to the coupon body and adapted for receiving an ultrasonic testing (UT) transducer; one or more UT transducers secured to the coupon holder member; an acoustic couplant positioned adjacent the one or more UT transducers; a sacrificial coupon connected to the coupon holder member such that the sacrificial coupon is adjacent the acoustic couplant; an attachment body for inserting the sacrificial coupon into a liquid or underground, dry environment; and a reference electrode either attached to or positioned adjacent to the coupon body for simultaneously measuring corrosion rate of the sacrificial coupon and an electromagnetic field created by an impressed current cathodic protection system.

A second aspect of the invention is a corrosion coupon probe including: a sacrificial coupon; one or more UT transducers; and an acoustic couplant, wherein the one or more transducers are connected to the sacrificial coupon and the acoustic couplant is positioned between the sacrificial coupon and the one or more UT transducers.

A third aspect of the invention is a corrosion monitoring system including: a corrosion coupon probe having (i) a sacrificial coupon, (ii) one or more UT transducers, and (iii) an acoustic couplant, wherein the one or more transducers are connected to the sacrificial coupon and the acoustic couplant is positioned between the sacrificial coupon and the one or more UT transducers; processing means for producing an excitation pulse, for receiving a transmitted pulse from the sacrificial coupon, and for processing signals to determine sacrificial coupon material thickness; and memory means for storing material thickness values determined by the processing means.

A fourth aspect of the invention is a separate wire that is welded to an aboveground or underground structure that is being protected and terminated at the at-grade, remote, test station for acquiring data for tracking and reporting.

A fifth aspect of the invention is the presence of a ground reference wire fastened to each of the underground, or under tank, coupons and terminated at the at-grade test station.

A sixth aspect of the invention is the presence of an above ground test station where all of the above-cited wires are terminated on separate test points along with the multi-pin connector containing the corrosion coupon probe UT transducer wires for receiving a transmitted pulse from the sacrificial coupon, and for processing signals to determine sacrificial coupon material thickness.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

FIG. 3 illustrates two potential operating locations of the test station;

FIGS. 4A-4E illustrate five modes of electrical to mechanical energy conversion used to characterize the amount of and type of material loss;

DETAILED DESCRIPTION

Figure 1:
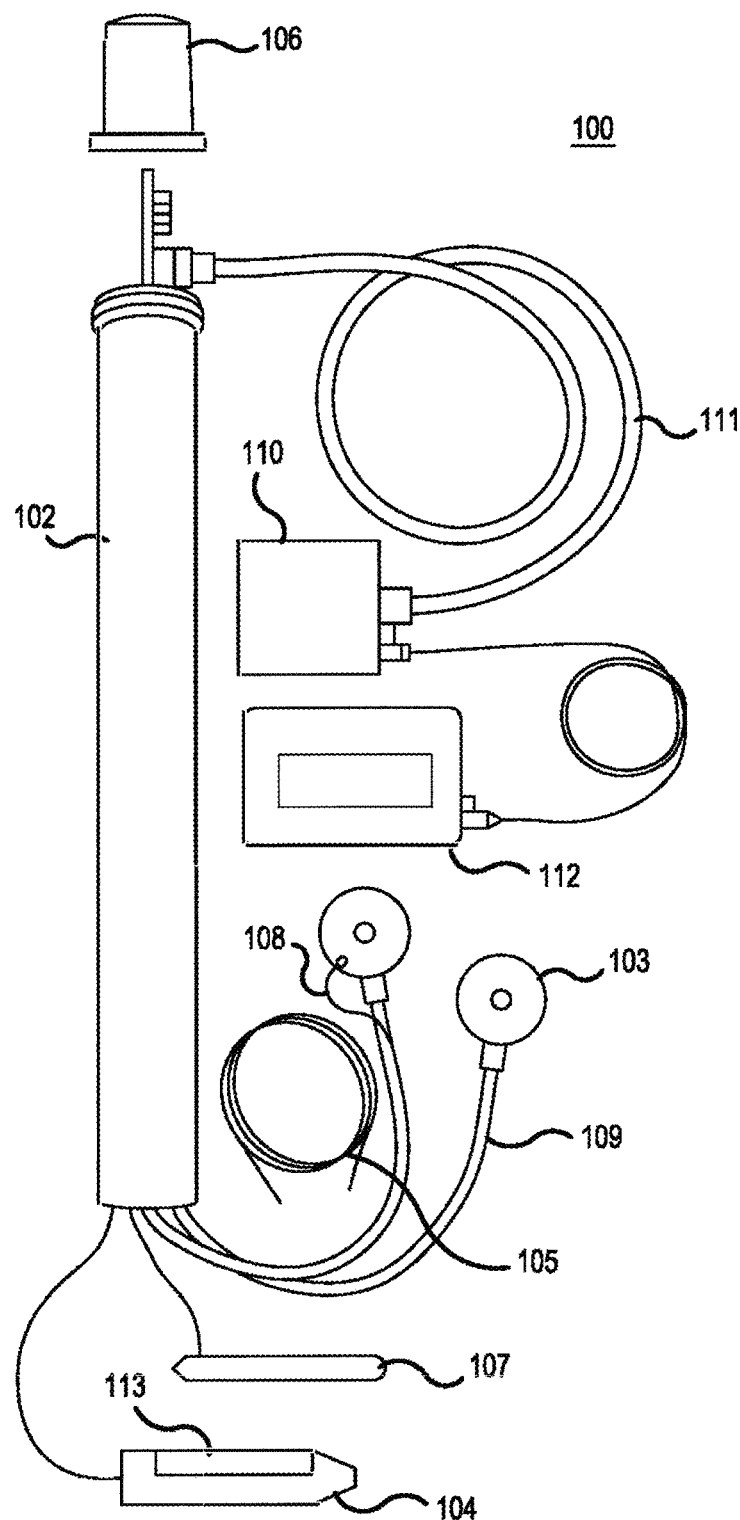
FIG. 1 is an exploded view of one of many possible embodiments of an ultrasonic cathodic protection test station.
Figure 2B:
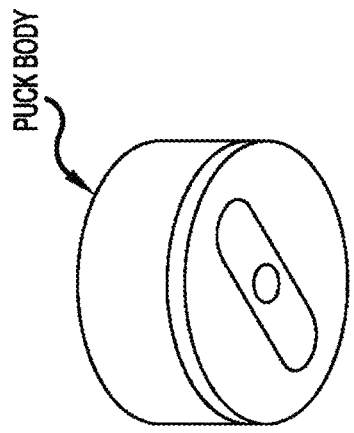
FIGS. 2A-2E illustrate one of many possible embodiments of an ultrasonic corrosion coupon.
Figure 2D:
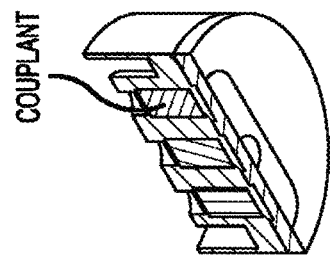
Figure 2E:
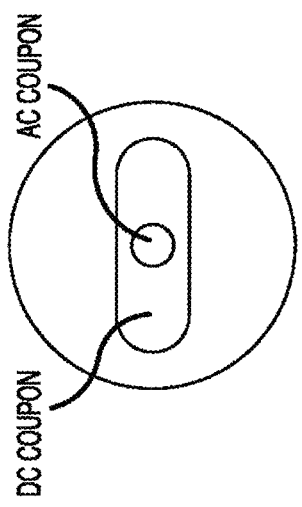
Figure 2A:
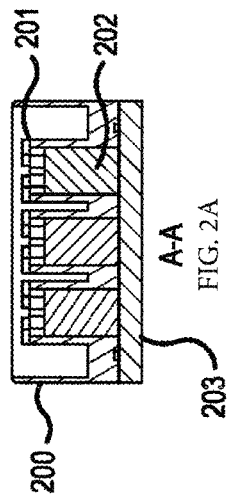
Figure 2C:
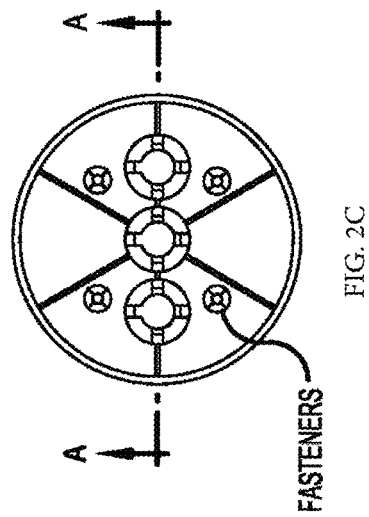

Referring generally to FIG. 1, there is shown an embodiment of an ultrasonic cathodic protection test station ("test station") 100 of the present invention. The test station 100 includes a mounting tube (:tube") 102 that is adapted for receiving sensor wires and/or transmitters, electrical components, and various connectors for configuring the tube 102 depending on the intended use of the test station 100. The tube 102 optionally but preferably includes a data I/O terminal 106, which optionally but preferably is detachably fastened to the tube 102.

Two or more ultrasonic coupons can be located via a cabling assembly at any distance from the test station tube 102. The shape of the coupon can be altered to fit the requirements of the environment that it is monitoring. In FIG. 1, two types of coupon bodies are shown. A round body 103 coupon preferably is used adjacent to, for instance, an underground pipeline. An elongated body 104 coupon can be used for use in aboveground storage tanks. A wire 105 is provided for attachment to an underground structure, in the case of a pipe, for instance, or for attachment to an above or below ground tank. The wire 105 is terminated at the I/O terminal 106. A reference electrode assembly 107 is connected to a cable assembly of any length that is terminated at the I/O terminal 106. Ground wires 108 and 109 are connected to each of the UT sacrificial coupons, e.g., 103, and terminated at the I/O terminal 106.

The test station 100 can include a data logger 110, which optionally but preferably contains software to pulse and acquire the UT information, prepare the data for subsequent analysis within the data logger, or transmit the data wirelessly to a remotely located receiver. The data logger 110 further can be used to organize the data within a database for future analysis. The data logger 110 can interface to any computer 112 via an input/output cable such as a USB cable.

The test station 100 can include an umbilical 111 in communication with the data logger 110, which optionally but preferably is interfaced with a general purpose computer or has independent processing means, and further includes a pulser/receiver unit. The umbilical 111 can transmit electrical energy, or pulses, created by the pulser/receiver in the data logger 110 to the test station coupons 103 or 104. The umbilical 111 also can transmit an electrical representation of the return signal from one more transducers in the test station 100 coupon 103 or 104 back to the data logger 110.

Referring generally to FIG. 2, there is shown one of many possible embodiments of an ultrasonic corrosion coupon transducer assembly ("transducer assembly") 200. The transducer assembly optionally but preferably has a body with one or more openings. A piezoelectric chip 201 can be positioned in each of the openings in the transducer assembly 200. For purposes of this invention, "piezoelectric chip" and "transducer" can be used interchangeably. In one of many possible alternative embodiments of the invention, the transducers 201 can be connected to a bottom surface of a coupon 203 by machine screws or other fastening means. An acoustic couplant 202 can be positioned within the transducer assembly 200 adjacent to the sacrificial coupon 203 and couplant 202. The acoustic couplants 202 are placed between the face of the piezoelectric chips 201 in the transducer assemblies 200 and the bottom surface of the coupon 203. As the machine screws or other fastening means are tightened, the couplants 202 are compressed to a fixed point that will not alter the quality of the UT transducer A-scan. The transducer assemblies 200 optionally but preferably are sealed and are waterproof so the assembly 200 can be positioned anywhere to monitor metal loss remotely using ultrasound as long as the wiring is properly sealed.

The coupon 202 material can be of one or more types of metal or non-metal that are subject to loss of integrity due to corrosion or erosion and where the loss and rate of loss can be precisely measured with the use of ultrasound transducers attached to the coupon material. In an alternative embodiment, the coupon material can be of one or more types of metal or non-metal that are subject to loss of integrity due to chemical attack and where the chemical attack can be associated with change in the exposed liquid product quality or a change in process conditions. In yet another alternative embodiment, the coupon material can be of one or more types of metal or non-metal that are subject to loss of integrity due to corrosion, erosion or chemical attack and where the electrical pulses of one or more transducers can be used to induce one or more different mechanical wave patterns which can be used to characterize the amount and type of material loss on the surface of the coupon material.

The ultrasonic corrosion coupon assembly 200 can be placed near or offset from a surface it is designed to monitor.

The ultrasonic corrosion coupon 203 is used as a surrogate to extrapolate the corrosion, pitting, metal loss, etc. of the pipe or other structure being monitored. The changes to the coupon 203 are representative of the changes to the pipe or other structure being monitored, and the condition of the structure being monitored can be determined indirectly by monitoring the status of the coupon 203 from the I/O terminal 106.

FIG. 3 shows two of the many possible locations for the placement of an ultrasonic cathodic protection test station 100. The test station 100 can be placed adjacent to a mechanical structure, such as an aboveground storage tank. The coupon 113 located on the elongated embodiment of a ultrasonic test station probe 114 can be used as a surrogate to extrapolate the corrosion, pitting, metal loss, etc. of the storage tank or other structure being monitored. The changes to the coupon 113 are representative of the changes to the underside of the tank, e.g., the condition of the tank floor or other structure being monitored can be determined indirectly by monitoring the status of the coupon 113. The probe 114 also can include a reference electrode 115, which can be used to measure potential difference of the impressed current impinging on the pipe or tank bottom, for instance, and ground. The data logger 116 contains software to pulse and acquire the UT information, prepare the data for subsequent analysis within the data logger, or transmit the data wirelessly to a remotely located receiver, and organize the data within a database for future analysis.

Figure 4B:
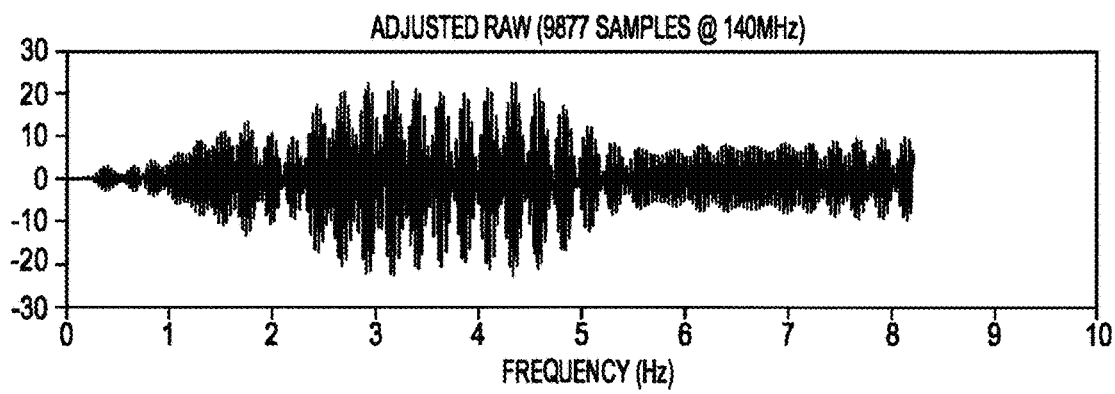

As shown in FIGS. 4A-4E, there are at least five modes of mechanical energy signal processing that may be applicable to the present invention. The first mode, shown in FIG. 4A, is created by the compression of the material directly under the UT transducer that reverberates from the front surface of the coupon to the back surface. The thickness of the coupon material can be determined by dividing the signal travel time from surface-to-surface in the coupon material by the speed of sound of the material.

The second mode, shown in FIG. 4B, of mechanical energy created by the UT transducer is referred to as a bulk wave. The bulk wave is created by one UT transducer, Transducer(i), that is received by the adjacent UT transducer, Transducer(ii), located a fixed distance from the transmitting UT transducer. The energy transmitted into the coupon material will change as a function of any change in the mechanical integrity of the coupon. Changes in mechanical integrity can be in the form of overall reduction in thickness, the appearance of localized pitting or the appearance of cracks. The total energy created by the bulk wave can be referred to as the root mean squared (RMS). The RMS value of a set of continuous-time waveforms is the square root of the arithmetic mean of the squares of the values, or the square of the function that defines the continuous waveform. The formula for a continuous function (or waveform) f(t) defined over the interval $T_1 \leq t \leq T_2$ is:

$$f_{rms} = \sqrt{\frac{1}{T_2 - T_1} \int_{T_1}^{T_2} [f(t)]^2 dt},$$

and the RMS for a function over all time is $$f_{rms} = \lim_{T \to \infty} \sqrt{\frac{1}{T} \int_0^T [f(t)]^2 dt}.$$

Figure 4C:
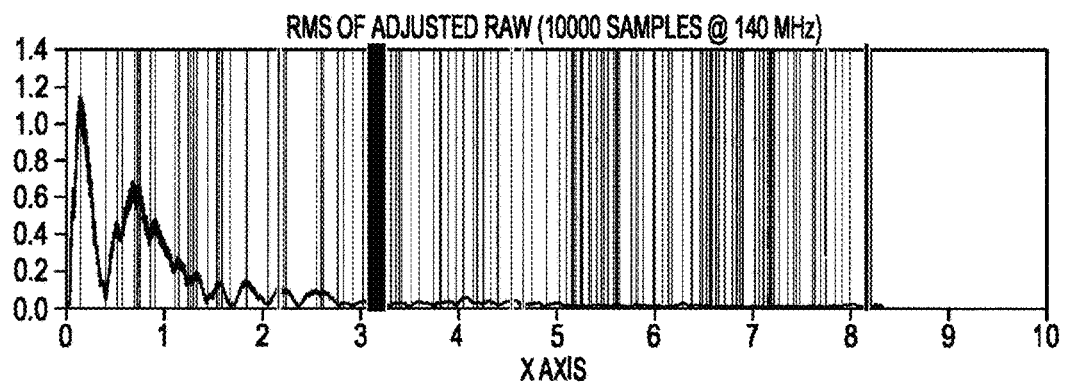
Figure 4D:
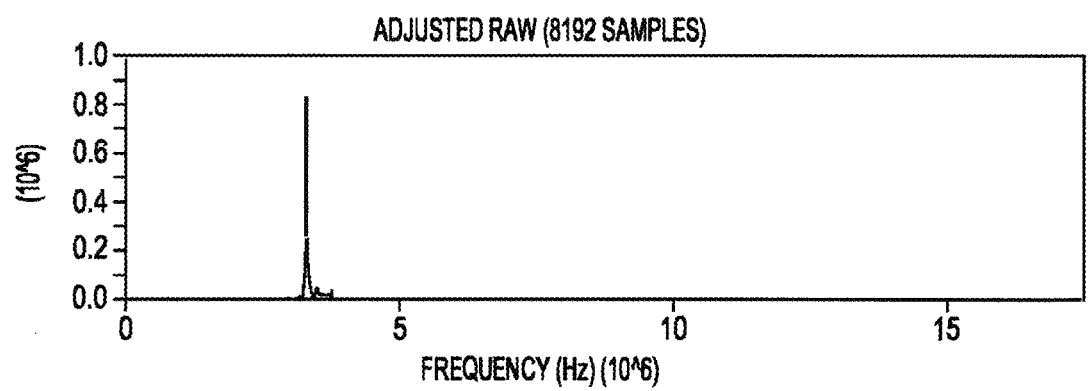

The effective RMS voltage (or power) of one or more sinusoids can be obtained without the use of calculus and can be calculated by squaring a waveform, taking the mean of the squared waveform and then computing the square root, as given by:

$$V_{rms} = \sqrt{\text{mean}[v(t)*v(t)]} = \sqrt{\frac{\text{area under the curve of } [v(t)*v(t)]}{\text{observation length}}}$$

where the observation length is the period, or integer multiple of the period, for as long as possible for the aperiodic signals generated by the piezoelectric-induced mechanical waves in the coupon. The total RMS value for any bulk wave can be measured and the resultant RMS return can be displayed as depicted in FIG. 4C.

An additional way to provide greater information about the current condition of the coupon and any change due to external factors is through the frequency response of the coupon. The total frequency response associated with the mechanical vibrations produced by the coupon as a result of the piezoelectric transducer, shown in FIG. 4D, can provide information about changes in the coupon's integrity. A fast Fourier transform (FFT) algorithm can be used to convert components of a signal, in this case mechanical vibrations, from its time domain to a representation in the frequency domain. There are a number of different types of FFT formulas but the most common one used for discrete Fourier analysis is noted below and is used in the current embodiment of the coupon-ultrasonic material measurement system:

$$X_k = \sum_{n=0}^{N-1} x_n e^{-i2\pi k \frac{n}{N}} \quad k = 0, \dots, N-1.$$

Figure 4E:
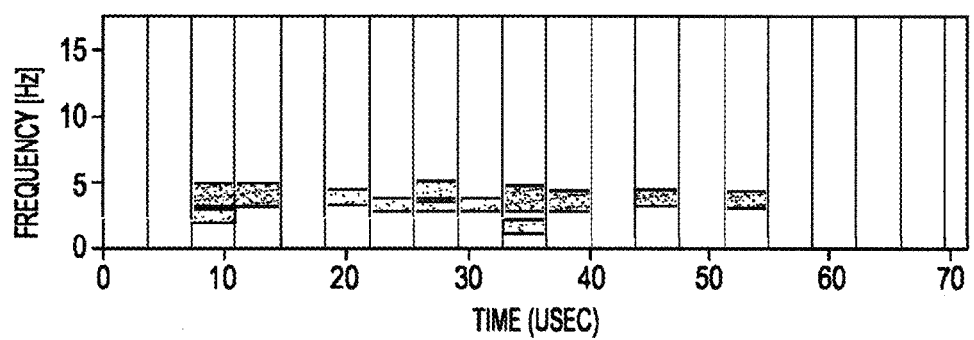

Finally, another method of detecting change in the integrity of the coupon is through the use of a spectrographic analysis as shown in FIG. 4E. In the this case, the mechanical energy resulting from the vibrations produced by the coupon as a result of the piezoelectric transducer can be displayed in terms of the coupons frequency response distributed over time.

Figure 5:
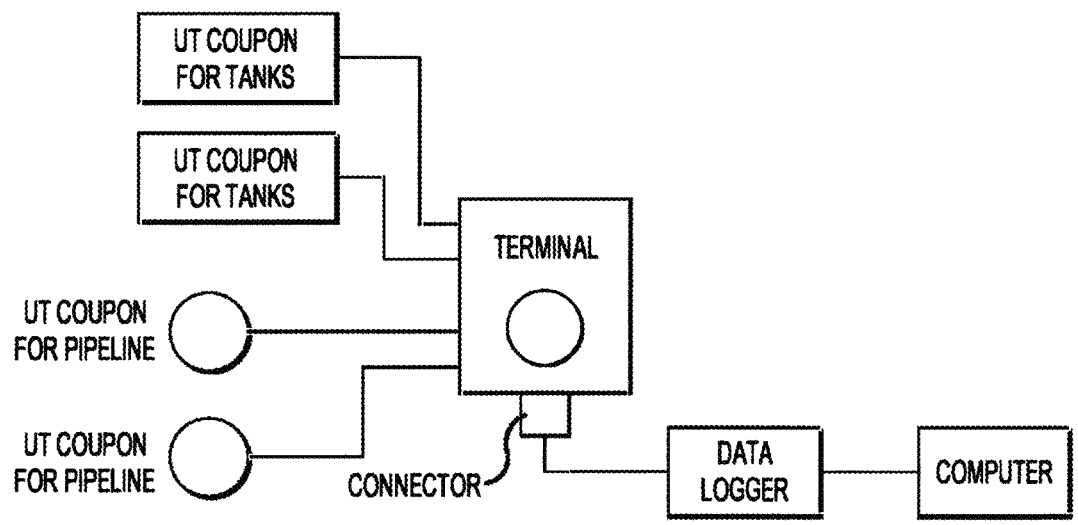
FIG. 5 is a block diagram of the total coupon probe inspection system showing the relationship between the data logger and the test station probe assembly.

FIG. 5 depicts the relationship of the components of a UT testing station. One or more coupons, e.g., a round coupon or an elongated coupon, depending on the structure to be monitored and its location, is communicably connected with an I/O terminal. The I/O terminal can be connected to a data logger, which optionally but preferably contains software to pulse and acquire the UT information, prepared the data for subsequent analysis within the data logger, or transmits the data wirelessly to a remotely located receiver. The data logger further can be used to organize the data within a database for future analysis. The data logger can interface to any computer via an input/output cable such as a USB cable.

Figure 6:
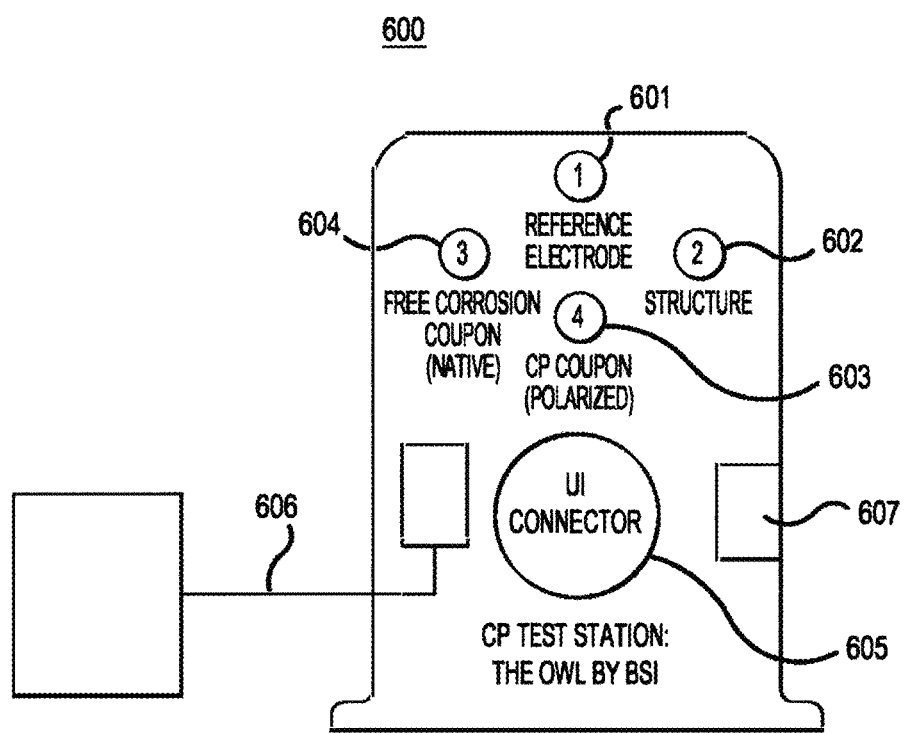
FIG. 6 illustrates the electrical terminals and connector for pulsing the UT transducers and receiving the UT data from the UT sacrificial coupons.

FIG. 6 shows one of many possible embodiments of an I/O terminal 600 with terminal connections: a reference electrode 601; a connection 602 to a wire connected to an underground structure; a connection 603 to an UT coupon located adjacent to the underground structure; a connection 604 to an UT coupon located further away from the underground structure; and one or more external electronic connectors 605 can be included and adapted for receiving an electronic connector extension cable 606 or an umbilical. An umbilical can be used as a conduit that houses wires necessary for providing electrical pulses to and from a pulser/receiver, which can be either attached to or located remotely from, a coupon-ultrasonic material measurement system of the present invention. A Radio Frequency Identification Device (RFID) 607 can be located onto the terminal I/O block 600.

CONCLUSION

While various embodiments of the present invention have been described above, it should be understood that they have been presented by way of example only, and not limitation. It will be understood by those skilled in the art that various changes in form and details may be made therein without departing from the spirit and scope of the invention. Thus, the breadth and scope of the invention should not be limited by any of the above-described exemplary embodiments.

What is claimed is:

1. A cathodic protection test station, comprising:
   a mounting tube having a top and a bottom;
   an input/output terminal secured to the top of the mounting tube;
   a transducer assembly having a body with one or more openings;
   one or more ultrasonic testing (UT) transducers positioned in the one or more openings in the transducer assembly;
   an acoustic couplant positioned adjacent the one or more UT transducers;
   a sacrificial coupon connected to the transducer assembly such that the sacrificial coupon is adjacent to the acoustic couplant; and
   a reference electrode connected to an input/output terminal with a wire for measuring corrosion rate of the sacrificial coupon.

2. The corrosion coupon probe of claim 1, wherein the reference electrode is a Cu—CuSO$_4$ grounding electrode.

* * * * *